US011435371B2

(12) United States Patent
Feitsma et al.

(10) Patent No.: US 11,435,371 B2
(45) Date of Patent: Sep. 6, 2022

(54) DEVICE, SYSTEM METHOD AND KIT FOR ISOLATING AN ANALYTE FROM A BODY FLUID SAMPLE

(71) Applicant: SIEMENS HEALTHINEERS NEDERLAND B.V., The Hague (NL)

(72) Inventors: Harma Martine Feitsma, Vught (NL); Vanda Lucia De Carvalho Vittorino De Almeida, Veldhoven (NL); Christianne Rossette Maria De Witz, Lommel (BE); Matthias Irmscher, Veldhoven (NL); Sandra Martina Van Den Bosch, Neunen (NL)

(73) Assignee: Siemens Healthineers Nederland B.V., The Hague (NL)

( * ) Notice: Subject to any disclaimer, the term of this patent is extended or adjusted under 35 U.S.C. 154(b) by 0 days.

(21) Appl. No.: 16/463,885

(22) PCT Filed: Nov. 23, 2017

(86) PCT No.: PCT/EP2017/080134
§ 371 (c)(1),
(2) Date: May 24, 2019

(87) PCT Pub. No.: WO2018/096005
PCT Pub. Date: May 31, 2018

(65) Prior Publication Data
US 2019/0383841 A1    Dec. 19, 2019

(30) Foreign Application Priority Data

Nov. 24, 2016 (EP) .................................... 16200545

(51) Int. Cl.
*G01N 35/00* (2006.01)
*G01N 33/543* (2006.01)
*G01N 33/569* (2006.01)
*G01N 30/60* (2006.01)

(52) U.S. Cl.
CPC ..... *G01N 35/0098* (2013.01); *G01N 30/6078* (2013.01); *G01N 33/54333* (2013.01); *G01N 33/5695* (2013.01)

(58) Field of Classification Search
CPC ......... G01N 30/6078; G01N 33/54333; G01N 33/5695; G01N 35/0098
See application file for complete search history.

(56) References Cited

U.S. PATENT DOCUMENTS

| 9,103,843 B2 * | 8/2015 | Nieuwenhuis ... G01N 33/54326 |
| 2010/0143883 A1 | 6/2010 | Wilson et al. |
| 2011/0065211 A1 * | 3/2011 | Nieuwenhuis ....... G01N 27/745 422/69 |
| 2012/0149021 A1 | 6/2012 | Yung et al. |

FOREIGN PATENT DOCUMENTS

| EP | 2168618 A1 | 12/2009 |
| EP | 3174976 A1 | 6/2017 |
| WO | 2010063293 A1 | 6/2010 |
| WO | 2014100456 A1 | 6/2014 |
| WO | 2015197659 A1 | 12/2015 |
| WO | WO2018005984 A1 | 1/2018 |

OTHER PUBLICATIONS

Liu et al., "Self-Contained, Fully Integrated Biochip for Sample Preparation, Polymerase Chain Reaction Amplification, and DNA Microarray Detection," Anal. Chem., 2004, vol. 76, No. 7, pp. 1824-1831.*
Gijs et al., "Microfluidic Applications of Magnetic Particles for Biological Analysis and Catalysis," Chem. Rev., 2010, vol. 110, No. 3, pp. 1518-1563.*
Creecy et al: "Tuberculosis Biomarker Extraction and Isothermal Amplification in an Integrated Diagnostic Device"; PLOS One, Jul. 2015, pp. 1-14.
Den Dulk: "Magneto-Capillary Valve for Integrated Biological Sample Preparation" Technische Universiteit Endhoven, 2011, 140 Page Document.
Den Dulk et al: "Magneto-Capillary Valve for Integrated Purification Enrichment of Nucleic Acids and Proteins"; Lab Chip, 2013, 13, 106, pp. 106-118.
Wang et al: "Bead Capture Increases the Sensitivity of Sputum Microscopy for the Diagnosis of Tuberculosis in Beijing, China"; Trans R Soc Trop Med Hyg, 3 Page Document, 2013.

* cited by examiner

*Primary Examiner* — Galina M. Yakovleva
(74) *Attorney, Agent, or Firm* — Dugan & Dugan, PC (57) ABSTRACT

The present invention relates to a device (100) for isolating an analyte (2) from a body fluid sample (4), wherein the analyte (2) is part of a target (6) contained in the body fluid sample (4). The device (100) comprises at least two types of magnetic particles (8, 12) for binding the analyte (2) and/or the target (6), at least three chambers (16, 18, 20) arranged in series to allow controlled movement of the magnetic particles (8, 12) and at least one fluid for releasing the analyte (2) from the target (6).

15 Claims, 4 Drawing Sheets

DEVICE, SYSTEM METHOD AND KIT FOR ISOLATING AN ANALYTE FROM A BODY FLUID SAMPLE

CROSS-REFERENCE TO PRIOR APPLICATIONS

This application is the U.S. National Phase application under 35 U.S.C. § 371 of International Application No. PCT/EP2017/080134, filed on Nov. 23, 2017, which claims the benefit of European Patent Application No. 16200545.8, filed on Nov. 24, 2016. These applications are hereby incorporated by reference herein.

FIELD OF THE INVENTION

The present invention relates to a device, a system a method and a kit for isolating an analyte from a body fluid sample, wherein the analyte is part of a target contained in the body fluid sample and, preferably, for detecting an analyte from a body fluid sample, e.g. DNA from a bacterium contained in sputum.

BACKGROUND OF THE INVENTION

In order to diagnose infections caused by microorganisms, like bacteria, the presence of the organism must be demonstrated by microscopy, culture or molecular methods such as PCR. Therefore, the microorganism has to be isolated. Although microscopy can be done directly from a body fluid sample, in practice, an isolating and concentration step of the microorganism is carried out before. Often there is an immediate need to identify the microorganism as well as certain information found in the nucleic acids contained in the microorganism, such as strain information or therapy resistances, to determine a proper course of treatment.

Tuberculosis (TB) is an infectious disease that kills millions of people each year despite the availability of potent anti-TB medications. Reduction in TB related morbidity and mortality is impeded by the lack of rapid and cost-effective diagnostic tests that are implementable in resource-limited settings. The disease is caused by the bacteria *Mycobacterium tuberculosis* (MTB), which mainly attacks the lungs, and is spread when an infected person coughs, sneezes or spits.

The most sensitive method of detecting MTB infection is amplification and/or detection of MTB DNA. This also enables detection of mutations that make MTB resistant to specific medications. However, these MDx assays require sufficient purification of the DNA before amplification/ detection, which requires expensive equipment and trained personnel.

Recently, magnetic beads have been developed with surfaces exhibiting specific bindings to nucleic acids. Therefore, some specific sequences of nucleic acids in a sample can be bonded to these functionalized surfaces of these magnetic beads. These magnetic beads can be for example used to purify nucleic acids from a sample or to remove other interfering components from a sample as disclosed in EP2128617A1.

Usually, automated or manual sample preparation protocols with magnetic beads employ the magnetic beads as a stationary phase when collected at a fixed magnet, such that the liquids required in the protocol can be exchanged. However, for integration in microfluidic cartridges, protocols with subsequential buffer exchange are inherently complicated, because they require liquid movement and hence pumps, closing valves and vents within the cartridge, which always leads to complex, high-cost cartridges. As a result, current microfluidic devices require extensive manual preparatory steps prior to introducing the sample into the device for subsequent isolation. Microfluidic devices by definition are designed to conduct reactions and process at a microfluidic scale.

Creecy, Amy et al. (PLoS One 10(7) (2015) 1-14) describe a sample preparation, wherein nucleic acids in a sample are adsorbed to the surface of silica coated magnetic beads. Next, nucleic acid extraction is achieved by pulling the magnetic beads using external magnets, wherein the magnetic beads were moved from a binding buffer solution to extraction solution. Later on, the nucleic acids are eluted for amplification.

The sample of choice for MTB diagnosis is sputum. Sputum is an extremely challenging matrix to extract DNA from, because of its high viscosity and high concentrations of interfering biomaterials, and the MTB bacterium is difficult to lyse. Sample preparation protocols for MTB are therefore more complicated than for other sample types such as swabs or blood. Before the binding step of DNA to silica beads, it is necessary to liquefy the sputum sample with liquefaction reagents and subsequently lyse the cells for releasing the DNA from *M. tuberculosis* bacteria. This step has not been integrated and requires additional manual handling steps.

SUMMARY OF THE INVENTION

Based on this background, it is an object of the present invention to provide a device, a system, a method and a kit which enables isolation of an analyte from a body fluid sample, wherein the analyte is part of a target contained in the body fluid sample and, preferably detection of an analyte from a body fluid sample in a fast manner in an integrated device. Therefore, the isolation of an analyte has to proceed without a time consuming pre-treatment. Another object of the invention is avoiding additional method steps.

In a first aspect of the present invention a device for isolating an analyte from a body fluid sample, wherein the analyte is part of a target contained in the body fluid sample is presented that comprises at least two types of magnetic particles, wherein a first type of magnetic particle is capable to bind a target to form a first complex for purifying the target from the body fluid sample, and wherein a second type of magnetic particle is capable to bind an analyte contained in the target to form a second complex for isolating the analyte, at least three chambers arranged in series and configured to include fluids, to allow controlled movement of the magnetic particles and to prevent the mixing of fluids, wherein a first chamber enables forming of the first complex by binding of the first magnetic particle to the target, wherein a second chamber enables releasing the analyte from the target and forming of the second complex by binding of the second magnetic particle to the analyte, and wherein a third chamber enables eluting the analyte from the second magnetic particle and isolating the analyte from the body fluid sample, an inlet for the introduction of the body fluid sample to one of the chambers, and at least one fluid for releasing the analyte from the target.

In a second aspect of the present invention a system for isolating an analyte from a body fluid sample, wherein the analyte is part of a target contained in the body fluid sample, said system is presented comprising a device for isolating an analyte from a body fluid sample, and a magnet for applying a magnetic field to controllably move the magnetic particles through the chambers.

In yet further aspects of the present invention, provided is a corresponding method for isolating an analyte from a body fluid sample, wherein the analyte is part of a target contained in the body fluid sample is presented comprising receiving a body fluid sample, wherein the body fluid sample comprises a target, which contains an analyte, and performing an isolation of an analyte from said body fluid sample by binding of a first type of magnetic particle to a target to form a first complex, moving the first complex from a first chamber to a second chamber, releasing the analyte from the target, binding of a second type of magnetic particle to an analyte to form a second complex, moving the second complex from a second chamber to a third chamber, and eluting the analyte from the second complex for isolating the analyte.

According to a further aspect, an embodiment of the present invention relates to a kit for isolating an analyte from a body fluid sample, wherein the analyte is part of a target contained in the body fluid sample, wherein the kit comprises at least two types of magnetic particles, wherein a first type of magnetic particle is capable to bind a target to form a first complex for purifying the target from the body fluid sample, and wherein a second type of magnetic particle is capable to bind an analyte contained in the target to form a second complex for isolating the analyte, at least one or more fluids which are selected from the group of buffer solutions, in particular liquefaction buffer, lysis buffer, wash buffer or elution buffer, and at least three chambers arranged in series and configured to include fluids, to allow controlled movement of the magnetic particles and to prevent the mixing of fluids, wherein a first chamber enables forming of the first complex by binding of the first magnetic particle to the target, or the first chamber enables receiving the first complex, wherein a second chamber enables releasing the analyte from the target and forming of the second complex by binding of the second magnetic particle to the analyte, and wherein a third chamber enables eluting the analyte from the second magnetic particle and isolating the analyte from the body fluid sample.

Preferred embodiments of the invention are defined in the dependent claims. It shall be understood that the claimed method, kit and system, have similar and/or identical preferred embodiments as the claimed device, in particular as defined in the dependent claims and as disclosed herein.

The device/system/kit and the method are based on the same concept, i.e. the isolation of an analyte from a body fluid sample by preparing the body fluid sample with the help of different types of magnetic particle, wherein these magnetic particles can be moved through different chambers. Explanations and embodiments described for the device/system/kit are therefore analogously valid for the method and vice versa.

The present invention is based on the idea to use different types of magnetic particles that specifically bind to a specific binding molecule to form a complex, wherein the complex can be moved through a series of stationary liquids for isolation an analyte from a body fluid sample. Before isolating the analyte, the target has to be activated to release the analyte.

The inventors have found that when using different types of magnetic particle for binding either an analyte or a target the isolation of an analyte which is part of a target can be isolated from body fluid sample in a single device respectively in at least three chambers, which are arranged in series. This offers the advantages over the current state of the art for preparing a body fluid sample. Therefore, the preparation can occur in a multistep approach in a fast manner. The present invention further more offers an isolation of analyte in low concentrations.

The term "analyte" as used herein, shall refer to any molecule of which concentration or presence as such is to be determined. Examples of analyte are biomarker such as proteins, peptides, hormones, DNA, RNA or enzymes. The "target" will typically be a microorganism of interest such as bacteria, viruses or cells. The analyte is part of the target; therefore the target includes the analyte such as nucleic acid. For isolating the analyte, the target has to be activated to release the analyte, i.e. by lysing the target or by activating the target to release the analyte without lysing itself.

The term "body fluid sample" is used in a broad sense herein and is intended to include a wide range of biological materials which contains target. The sample may be any suitable fluid of biological origin in which the analyte is part of the target, for example a droplet of blood, sputum or urine.

In the context of the present invention the body fluid sample is not limited to a crude sample from a subject, but may rather comprise further reagents such as buffer reagents. In a preferable embodiment, the body fluid sample may be mixed with a buffer solution, in particular a liquefaction buffer before the body fluid sample is introduced into the chambers.

The term "particle" as used herein means a small, localized object to which can be ascribed a physical property such as volume or mass. In the context of the present invention a particle comprises or consists of any suitable material known to the person skilled in the art, e.g. the particle may comprise, or consist of, or essentially consist of inorganic or organic material. Typically, a particle may comprise, or consist of, or essentially consist of metal or an alloy of metals, or an organic material, or comprise, or consist of, or essentially consist of carbohydrate elements. Examples of envisaged material include agarose, polystyrene, latex, polyvinyl alcohol, silica and ferromagnetic metals, alloys or composition materials. Particularly preferred are magnetic or ferromagnetic metals, alloys or compositions. Particularly preferred particles useful in the present invention are superparamagnetic particles.

The term "superparamagnetic" as used herein describes a form of magnetism, which appears in small ferromagnetic or ferromagnetic nanoparticles. It is known in the art that in sufficiently small nanoparticles, magnetization can randomly flip direction under the influence of temperature. The time between two flips is referred to as the Néel relaxation time. In the absence of an external magnetic field, when the time used to measure the magnetization of the nanoparticles is much longer than the Néel relaxation time, the magnetization appears to be in average zero, i.e. in the paramagnetic state. In such a state an external magnetic field is able to magnetize the nanoparticles similarly to a paramagnet. However, the magnetic susceptibility is much larger than those of paramagnets. In further preferred embodiments, the material may have specific properties. The material may, for example, be magnetic or be non-magnetic. The material may, in other embodiments, be hydrophobic, or hydrophilic. In further specific embodiments the particle is a plastic particle. Examples of plastic particles include latex or polystyrene beads, i.e. those commonly used for purification.

The term "magnetic particle" as used herein, shall refer to permanently magnetic particles and/or magnetizable particles, for example supermagnetic particles. The size of these magnetic particles typically ranges between 3 nm and 50 µm.

The binding between the magnetic particle and the analyte or target in a complex may be a physical binding (i.e. adhesion) or preferred a chemical binding (i.e. by hybridization or specific covalent binding).

Recently, magnetic beads have been developed that can specifically bind MTB and related bacteria, because of a hydrophobic coating (Xiaobo Wang et al., "Bead capture increases the sensitivity of sputum microscopy for the diagnosis of tuberculosis in Beijing, China"—Royal Society of Tropical Medicine and Hygiene 107(11), September 2013). It has been found by the inventors that the first magnetic particle may be employed to bind MTB bacteria and extract them e.g. from a sputum sample, such that subsequent lysis and extraction of DNA with the second magnetic particle may be started from a cleaner solution.

In a preferable embodiment, the magnetic particles may be beads with a particular surface coating or the like for a specific binding of the analyte or target. The magnetic particles may comprise at least one of the following surface molecules or atoms (and/or fractions and/or aggregates thereof) to which of the analyte or target can bind or with which they can react in another way: proteins and/or fractions and/or aggregates thereof, in particular streptavidin and/or antibodies that bind specifically to the analyte or target; nucleic acids and/or fragments and/or aggregates thereof (e.g. DNA, RNA, aptamers); enzymes (e.g. proteases); electrically charged molecules or atoms to bind unspecifically to oppositely charged analyte or target; silica molecules; metal atoms such as gold atoms; hydrophobic or hydrophilic layers (e.g. polymers).

The magnetic particle may be stored anywhere in the device (e.g. in the chambers) and may be moved through the device by a magnetic force, preferably from the first and second chambers to the second and third chambers, wherein they may bound to the target or the analyte.

In a preferable embodiment the body fluid sample may be incubated with the first magnetic particle for form the first complex in the first chamber.

In a preferable embodiment, the magnetic particles may be provided in the chambers prior to the introduction of the sample or may be provided in an additional chamber, called "magnetic particle storage", wherein the magnetic particle storages are connected to the chambers. The different storages may prefer coupled to the chambers via valve, e.g. a magneto-capillary valve (MCV). This allows a controlled transfer of the magnetic particle from the storage into the first, second or third chamber. The magnetic particles may for example be stored in dried form or solved in a fluid.

In a preferable embodiment the magnetic particle may be stored separately from the chambers, e.g. in "sample preparation chambers". This sample preparation chamber may not be connected to the chambers. Therefore, the chambers, in particular the first chamber, may be configured to receive the body fluid sample incubated with the magnetic particle. In this case the first complex may be formed in the sample preparation chamber before introducing into the chambers. Therefore, the incubation may be performed under controlled conditions. This embodiment advantageously enables the forming of the first complex in a bigger volume than in the first chamber.

The magnetic particles may particularly comprise magnetizable beads. Therefore, the magnetic particles can controllably be moved by magnetic means, for example by a magnetic field generator such as a permanent magnet. The magnetic particle may particularly actively be moved under the control of a user or of an apparatus. The magnetic particle may for example be moved by magnetic or electrical effectors or means, wherein such means are preferably comprised by the system.

The chambers according to the invention are arranged in series and are preferably designed as microfluidic chambers for the accommodation and processing of small amounts of fluids (sample and solutions). The chambers are generally connected in such a way that the magnetic particle (with or without bound target or analyte) can controllably moved. The cambers may not be limited to three chambers.

In a preferable embodiment the chambers may configured to have further inlets, for introducing fluids, magnetic particles etc.

According to the invention the device and kit typically comprises, additionally to the above mentioned components, further chambers, channels, inlets, outlets, valves and/or pumping elements etc. The device and kit may further comprise means for amplification, e.g. for amplify nucleic acid. Preferred amplification means are those which can be used for PCR such as LAMP. Therefore, the system has to be adjusted.

The device and the kit of the present invention may be typically in form of an inexpensive, disposable cartridge intended for a single isolation of an analyte from a body fluid sample, e.g. a disposable microfluidic cartridge (a "lab on a chip"). Such device is exceptionally well suited for running rapid an isolation of an analyte and preferably a detection of an analyte. Thus, the device and the kit of the present invention establish a solid basis for reliable point-of-care diagnostics by relatively untrained personnel, although it could be used in larger formats in clinical laboratory settings as well.

In a preferable embodiment, the chambers are connected via magneto-capillary valves through which the magnetic particles can controllably be moved.

The term "magneto-capillary valves" (MCV) as used herein shall refer to i.e. an element or component that is disposed between two chambers and through which magnetic particles can be moved by magnetic forces. A central area of this MCV is typically repellent for the fluids that are processed (e.g. hydrophobic if aqueous liquids are processed). Fluids of the adjacent chambers will therefore not cross the valve and mix, but magnetically responsive substances, e.g. magnetic beads, can actively be transferred through the valve by the application of magnetic forces.

MCV are well known in the art and are amply described in the scientific and patent literature, for example Remco et al. "Magneto-capillary valve for integrated purification and enrichment of nucleic acids and proteins", Lab Chip, 2013, 13, 106 or WO 2015/197659.

In another preferable embodiment, the device further comprises one or more fluids which are selected from the group of buffer solutions, in particular liquefaction buffer, lysis buffer, wash buffer or elution buffer.

The term "buffer solutions" may generally be understood as a plurality of reagents that have a pH stabilizing effect and preferably define an osmotic friendly solution.

In particular a "liquefaction buffer" may generally be understood as a plurality of reagents that is designed for the liquefaction of viscous body fluid sample e.g. sputum sample. Therefore, the sample is homogenized. A preferred liquefaction buffer may comprise N-acetyl-L-cysteine-sodium hydroxide (NALC-NaOH).

In a preferable embodiment, the body fluid sample is incubated with the liquefaction buffer before entering to the chambers, in particular when using the kit.

The term "lysis buffer" may be generally understood as a plurality of reagents that is used for the purpose of breaking open cells. When using lysis buffer DNA, sugars and other compartments of the cell are combined in the so called lysate. Therefore, compartments of cells may be extracted from the remaining lysate, e.g. isolating DNA of a bacterium. A preferred lysis buffer may be a lysis/binding buffer and e.g. comprise Tris-HCl, GuSCN, Triton X-100 and may have a pH value of 6.4 to 7.6.

The term "wash buffer" may generally be used for cleaning up a sample e.g. for cleaning up the complex of bound magnetic particle and the target or analyte. A preferred wash buffer may comprise glycine-HCl and may have a pH value of 3.5.

The term "elution buffer" may generally be understood as a plurality of reagents that may be used for splitting up the complex into the components of e.g. magnetic particle and analyte. A preferred elution buffer may comprise Tris-HCl and may have a pH value of 8.5.

The different properties of the buffer solutions enable a fast process of isolating an analyte. The buffer solutions may therefore be stored in the chambers or in fluid storages next to the chambers in series in a useful order. Such order is known to the person skilled in the art.

This embodiment advantageously enables an isolation of an analyte in the device without any preparation of the device by a user. Otherwise the user of the device may have to fill the required fluids into the chambers before using the device, especially before the introduction of the body fluid sample into the inlet of the device.

The buffer solution may also be stored separately from the chambers. The user can thus fill these buffer solutions into the chambers or in fluid storages next to the chambers when using the kit or the device.

In yet another preferable embodiment, the device further comprises fluid storages connected to the chambers for storing fluids and/or magnetic particles.

This embodiment advantageously enables the controlled flowing of the fluids into the chambers when needed. This embodiment further advantageously prevents an outflow of the fluids from the device.

According to a preferred embodiment of the present invention, the fluid storage is a blister containing the fluids and optionally the magnetic particles and is rupturable for discharging the fluid to the chambers. A blister may be produced easily and inexpensive while providing for a desired and defined breaking point of the blister for expelling the fluid into the chambers. Otherwise the fluids and optionally the magnetic particles can be released from the blister by piercing it under the application of pressure.

In another preferable embodiment, at least one fluid is a lysis buffer for lysing the target to release the analyte stored in the second chamber and/or in a fluid storage connected to the second chamber.

This embodiment advantageously enables the lysing of the target inside the chamber. This embodiment further advantageously enables the releasing of the analyte, when the target is solved in the lysis buffer i.e. bound as a first complex with the first magnetic particle. Thus, the analyte may bind to the second magnetic particle when available in the second chamber to form the second complex comprised the analyte and the second magnetic particle.

In a preferable embodiment, the first magnetic particles are stored in the first chamber or in a fluid storage connected to the first chamber and/or wherein the second magnetic particles are stored in the second chamber or in a fluid storage connected to the second chamber.

This embodiment advantageously enables the rapid and effective isolation of an analyte from a target from a body fluid sample, since the magnetic particle are in the chambers wherein they bind to the analyte or the target or being close to the chambers where they form the first and second complex and can be moved fast into these chambers.

In another preferable embodiment, the analyte is selected from the group of cell components such as proteins, antibodies, lipids, enzymes, nucleic acids such as DNA or RNA, and any mixture thereof.

This embodiment advantageously enables the isolation of e.g. DNA of a bacterium. This is advantageous since mutations of the cell components may be detected. This may be useful if the isolation of the analyte is performed for diagnostic reasons. Therefore, the isolation of the analyte leads to a proper course of treatment. In addition, isolation of an analyte such as nucleic acids may enable amplification thereof.

In a preferable embodiment, the target is selected from the group of cells, viruses, bacteria in particular *M. tuberculosis*.

This embodiment advantageously enables the isolation of cells, viruses, bacteria or *M. tuberculosis* as well as their components (analyte). The isolation of components in such bacteria and also in the above listed group may be used in diagnostic methods. For example *M. tuberculosis* is a pathogenic bacterial and the causative agent of tuberculosis. A separation of *M. tuberculosis* and a subsequent isolation of e.g. *M. tuberculosis* DNA advantageously enable the determination of drug resistance strain and therefore enable an appropriate medical treatment.

In another preferable embodiment, the magnetic particles have a coating for specific binding to a target, such as a hydrophobic coating for binding *M. tuberculosis*, or a silica coating for binding nucleic acids.

This embodiment advantageously enables the binding of *M. tuberculosis* bacteria, micro-organisms having a hydrophobic surface and nucleic acids.

Optionally, said hydrophobic bead comprises a long hydrocarbon chain bearing multiple polar, e.g. ionic sites. Said multiple polar or ionic sites may be located together at one portion, e.g. an end portion, of the chain or may be spaced along said chain as they are in p-DADMAC.

The hydrophobic bead may be anionic but preferably is cationic, as in the case of p-DADMAC and preferably is poly-diallydimethyl ammonium chloride (DADMAC) itself. Since most bacterial cells are negatively charged the effect of p-DADMAC binding to the mycobacterial waxy coat is that the cells are converted to a net positive charge. This is advantageous as it ensure that other organisms that do not bind p-DADMAC remain negatively charged and so do not become bound to the complex. In addition, organisms that are not sufficiently hydrophobic will not bind to p-DADMAC coated surfaces, thus giving a degree of selectivity of the type of organism capture.

In a preferable embodiment, the body fluid sample is selected from the group of sputum, blood, plasma, serum, lactation products, amniotic fluids, saliva, urine, semen, cerebrospinal fluid, bronchial aspirate, perspiration, mucus, liquefied stool sample, synovial fluid, lymphatic fluid, tears, tracheal aspirate, and any mixture thereof.

This embodiment advantageously enables an isolation of different types of analyte of a broad spectrum of body fluid sample.

In another preferable embodiment, the device further comprises a fourth chamber, in which the first and/or second complex can be washed. This embodiment advantageously enables a purification of the complex and lead to a separation of an analyte in a pure manner.

In another preferable embodiment, the system further comprises a detection unit for detecting the magnetic particles bound to the target or analyte, wherein the detection unit preferably detects the analyte bound to the second magnetic particle.

The above mentioned "detection unit" may particularly comprises optical means, wherein these means may comprise a light source such as a laser or an LED with which spots in the fluid that comprises the magnetic particles bound as a complex and can be illuminated. The detection can be ensured by any direct or indirect method known in the art. Particular detection methods are based on the magnetic properties of the particle such as GMR or on optical properties of the magnetic particles, such as detection with frustrated total internal reflection.

The detection may be performed by scanning the liquid sample in a plane obliquely oriented with respect to the main plane of the chamber wherein the detection of the complex may be performed. Those detection technics are well known in the art and are amply described in the patent literature (e.g. in WO 2010/063293).

For the detection, the magnetic particle may comprise a label. As used herein, the term "label" refers to a composition capable of producing a detectable signal indicative of the present of a bound target or bound analyte. Suitable labels include fluorescent molecules, radioisotopes, nucleotide chromophores, enzymes, substrates, chemiluminescent moieties, bioluminescent moieties, and the like. As such a label is any composition detectable by spectroscopic, photochemical, biochemical, immunochemical, electrical, optical or chemical means. For example, the magnetic particle can be labeled with a detectable tag such as c-Myc, HA, VSV-G, HSV, FLAG, V5, or HIS, which can be detected using an antibody specific to the label for example, an anti-c-Myc antibody.

Exemplary fluorescent labels have a fluorescence absorption in the wavelength region between 300 and 800 nm. Fluorescent labeling is the process of covalently attaching a fluorophore to another molecule, such as a protein or nucleic acid. For example, the fluorescent labels include, but are not limited to, Hydroxycoumarin, Succinimidyl ester, Aminocoumarin, Methoxycoumarin, Cascade Blue, Hydrazide, Pacific Blue, Maleimide, Pacific Orange, *Lucifer* yellow, NBD, R-Phycoerythrin (PE) or conjugates thereof, Fluor X, Fluoresceinisothyocyanate (FITC), BODIPY-FL, TRITC, X-Rhodamine (XRITC), Allophycocyanin (APC) or conjugates thereof, Alexa Fluor.

Many quantitative techniques are known to harness the unique properties of fluorescence including: direct fluorescence measurements, fluorescence resonance energy transfer (FRET), fluorescence polarization or anisotropy (FP), time resolved fluorescence (TRF), fluorescence lifetime measurements (FLM), fluorescence correlation spectroscopy (FCS), and fluorescence photobleaching recovery (FPR).

In another preferable embodiment, the kit further comprises a sample preparation chamber, wherein the sample preparation chamber enables forming of the first complex by binding of the first magnetic particle to the target in the body fluid sample.

In a preferable embodiment, the sample preparation chamber may comprise the first magnetic particle. This embodiment advantageously enables a separate incubation of the body fluid sample with the first magnetic particle to form the first complex. This embodiment further advantageously enables pre-preparation of the body fluid sample in the sample preparation chamber e.g. a liquefaction of the sample. Further, this embodiment advantageously enables incubation under controlled conditions and optionally in a bigger volume.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
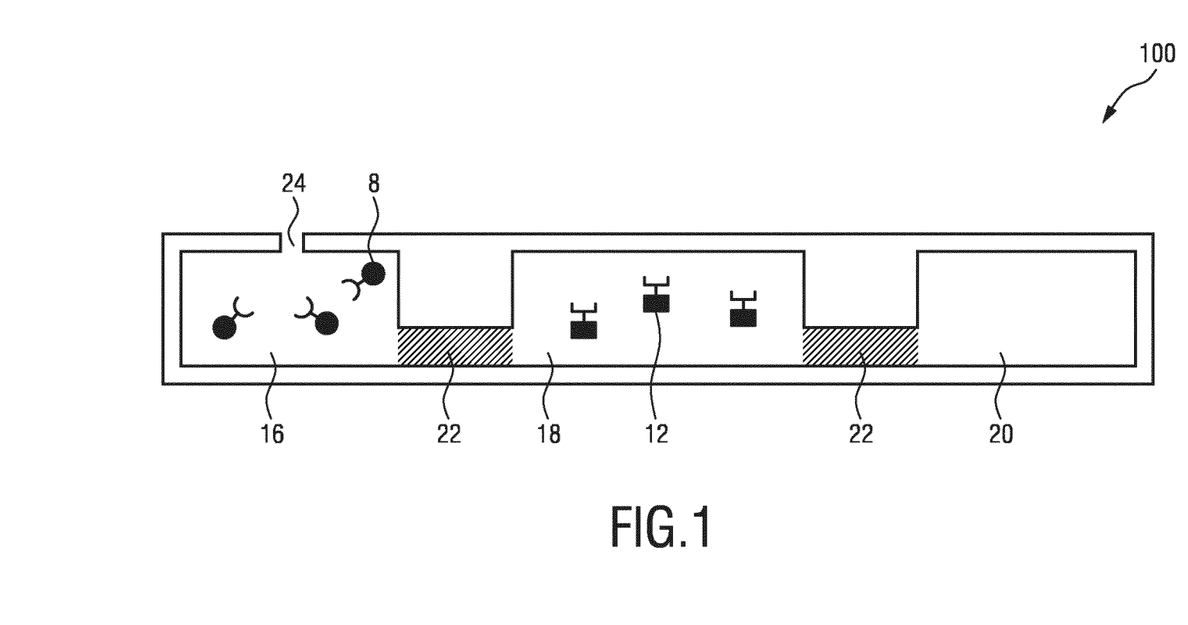
FIG. 1 shows a first embodiment of a device in accordance with the present invention.

FIG. 1 shows a first embodiment of a device 100 in accordance with the present invention. The device 100 shown in FIG. 1 comprises a sample inlet 24 for receiving a body fluid sample 4. Besides the sample inlet 24 the device 100 further comprises a first, a second and a third chamber 16, 18 and 20, wherein these chambers are connected via valves, preferable magneto-capillary valves 22.

In a preferable embodiment the first chamber 16 may comprise the first magnetic particle 8 and the second chamber 18 may comprise the second magnetic particle 12. In a further preferable embodiment of the present invention the magnetic particles are not stored in the chambers 16 and 18, either in magnetic particle storages, wherein these storages are arranged next to the chambers 16 and 18 (see also FIG. 3).

The device 100 may further comprise fluids, wherein at least one fluid is for releasing the analyte 2 from the target 6 (not shown).

In a further preferable embodiment of the present invention the device 100 may comprise a liquefaction buffer in the first chamber, a lysis buffer in the second chamber and an elution buffer in the third chamber (not shown). Therefore, the isolation of the analyte 2 may be performed with the following steps (see also FIG. 4):

In a first step the body fluid sample 4 e.g. sputum is introduced into the device 100. If the body fluid sample 4 is filled in the first chamber 16, the body fluid sample 4 may be homogenized and liquefied by the liquefaction buffer. Subsequently, the first type of magnetic particle 8 may bind to the target 6 to form a first complex 10. The target 6 is part of the body fluid sample 4, wherein an analyte 2 is again part of the target 6. After an incubation time most of the first magnetic particle 8 are present as a first complex 10.

In a second step the first complex 10 is moved form the first chamber 16 to the second chamber 18 by a magnet 32 through the valve 22, wherein the second magnetic particle 12 can be stored. When the first complex 12 reaches the second chamber 18, wherein the lysis buffer may be stored, the target 6 bound to the magnetic particle 8 may lyse and thereby release the analyte 2. Alternatively, the fluid for releasing an analyte 2 may be stored in a chamber closed to the second chamber 18 (see also FIG. 3). If the analyte 2 is solved in the buffer solution contained in the second chamber 18, the analyte 2 may bind to the second magnetic particle 12 to form a second complex 14. After a further incubation time most targets 6 are lysed and most analyte 2 are bound as a second complex 14.

Alternatively, in a not shown embodiment, the first complex 10 may be moved from the first chamber 16 to a washing chamber, wherein the washing chamber is arranged between the first chamber 16 and the second chamber 18. In this washing chamber the complex 10 can be washed e.g. in a wash buffer and afterwards may be moved to the second chamber 18 (not shown).

In a following step the second complex 14 may be moved from the second chamber 18 to the third chamber 20. In a preferable embodiment a washing chamber 30 is arranged between the second and third chamber 18 and 20 for washing the second complex 14. In the third chamber 20 the analyte 2 is eluted from the magnetic particle 12 for isolating the analyte 2. Therefore, the elution buffer may be stored in the third chamber 20 or in a fluid storage connected to the third chamber. In a preferable embodiment the analyte 2 may be detected by a detection unit 34. The detection may be performed either by detecting the analyte 2 or by detecting the analyte 2 bound to the second magnetic particle 12 before eluting.

The isolated analyte 2 filled in the third chamber 20 may be further used for amplifying or analyzing the analyte 2. In a preferable embodiment the third chamber 20 is arranged for analyzing the analyte 2. For example the third chamber 20, or any other chamber arranged behind the second chamber 18, comprises one or more binding spots on its inner surface. The binding spots comprise binding sites to which the second complex 14 can bind. This binding can in turn be detected with appropriate surface specific detection procedures such as frustrated total internal reflection. Alternatively, the third chamber 20 is arranged to perform a detection assay inside.

Figure 2:
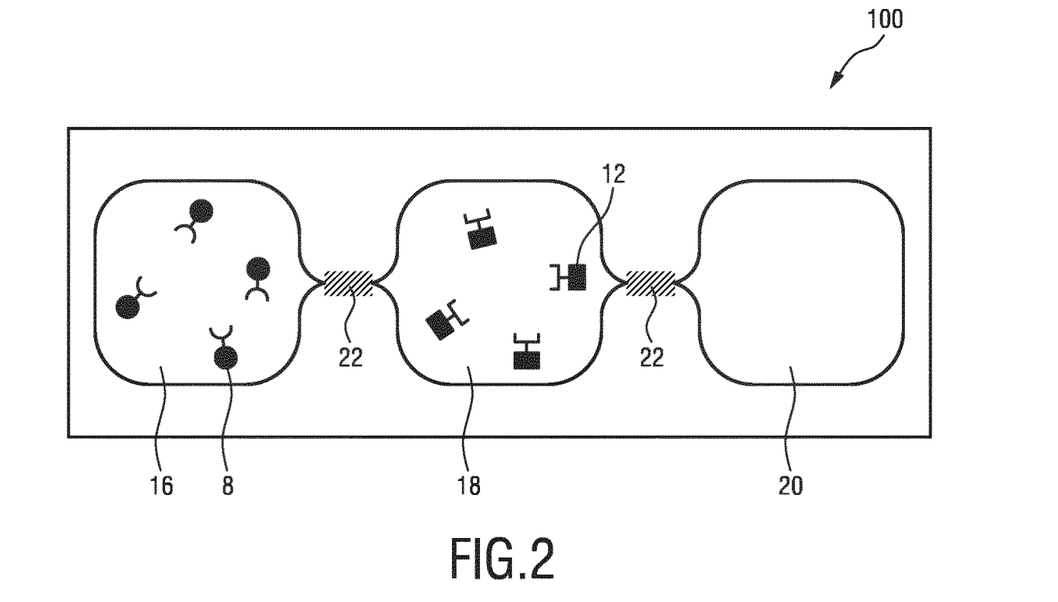
FIG. 2 shows the first embodiment of a device from a different view in accordance with the present invention.

FIG. 2 shows the first embodiment of the device 100 from a different view in accordance with the present invention. The FIG. 2 schematically shows a top view onto the device 100 shown in FIG. 1.

FIG. 2 shows the magneto-capillary valve technology. Therefore, the chambers are arranged in a way that liquids, which may be stored in the chambers 16, 18 or 20, are stationary and can not be mixed with each other, because of the MCV 22. Rather than moving fluids in this device 100, discrete chambers of fluids are present at fixed positions in the device 100 and magnetic particles 8 and 12 are actuated between the fluids. The MCV concept is characterized by the use of two planar surfaces at a capillary mutual distance, with specific features to confine the fluids by capillary forces, and the use of a gas or a phase-change material separating the stationary fluids. MCV are well known in the art and are amply described in the scientific and patent literature (Remco C. den Dulk, Kristiane A. Schmidt, Gwenola Sabatte', Susana Liébana, Menno W. J. Prins: "Magneto-capillary valve for integrated purification and enrichment of nucleic acids and proteins", Lab Chip, 2013, 13, 106).

In a preferable embodiment the valves 22 are configured as an air valve. This technology allows for low-cost integrated cartridges, as the only moving part is the external magnet.

The device 100 is preferable in form of an inexpensive, disposable cartridge intended for a single isolation of an analyte 2 from a body fluid sample 4, e.g. a disposable microfluidic cartridge (a "lab on a chip"). The device 100 may be made of any kind of material as long as it is compatible with the isolation to be performed on the body fluid sample 4. Preferred materials are glass or plastic by injection molding especially in view of disposability of such device 100 and/or cost during production. The main function of the device 100 is to provide an inlet in which isolation can be performed.

Figure 3:
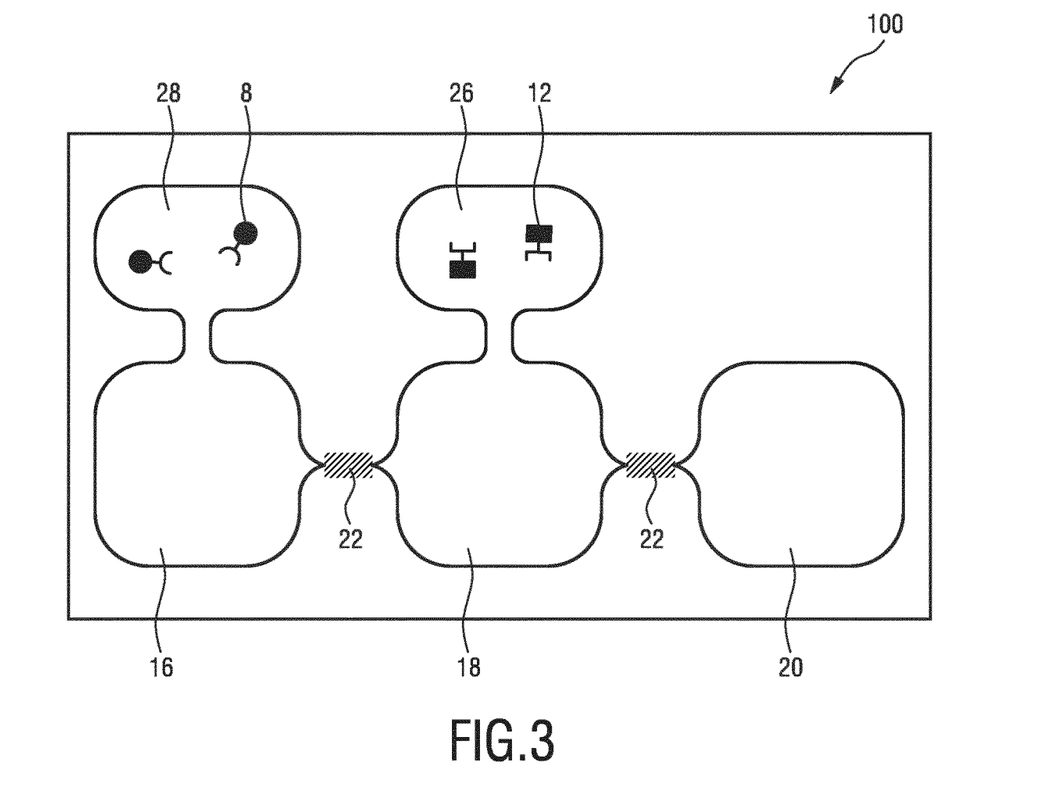
FIG. 3 shows a second embodiment of a device in accordance with the present invention.

FIG. 3 shows a second embodiment of a device 100 in accordance with the present invention. In addition to the elements of the first embodiment of the device 100 shown in FIGS. 1 and 2 the second embodiment of the device 100 further comprises the storages 28 and 26, wherein the magnetic particles 8 and 12 are stored.

In a preferable embodiment the storages 26 and 28 are arranged as fluid storages, wherein fluids may be stored as well as magnetic particles 8 and 12. If these chambers containing fluids the connecting valves between the chambers 28 and 16 and 26 and 28 are permeable for the fluids. If the storages only contain magnetic particles, the valves may be configured as a MCV.

In a preferable embodiment the magnetic particle 8 and 12 may be stored in the same chambers or storages. This is possible because of the specific binding affinity of the magnetic particles to the target or analyte.

Figure 4:
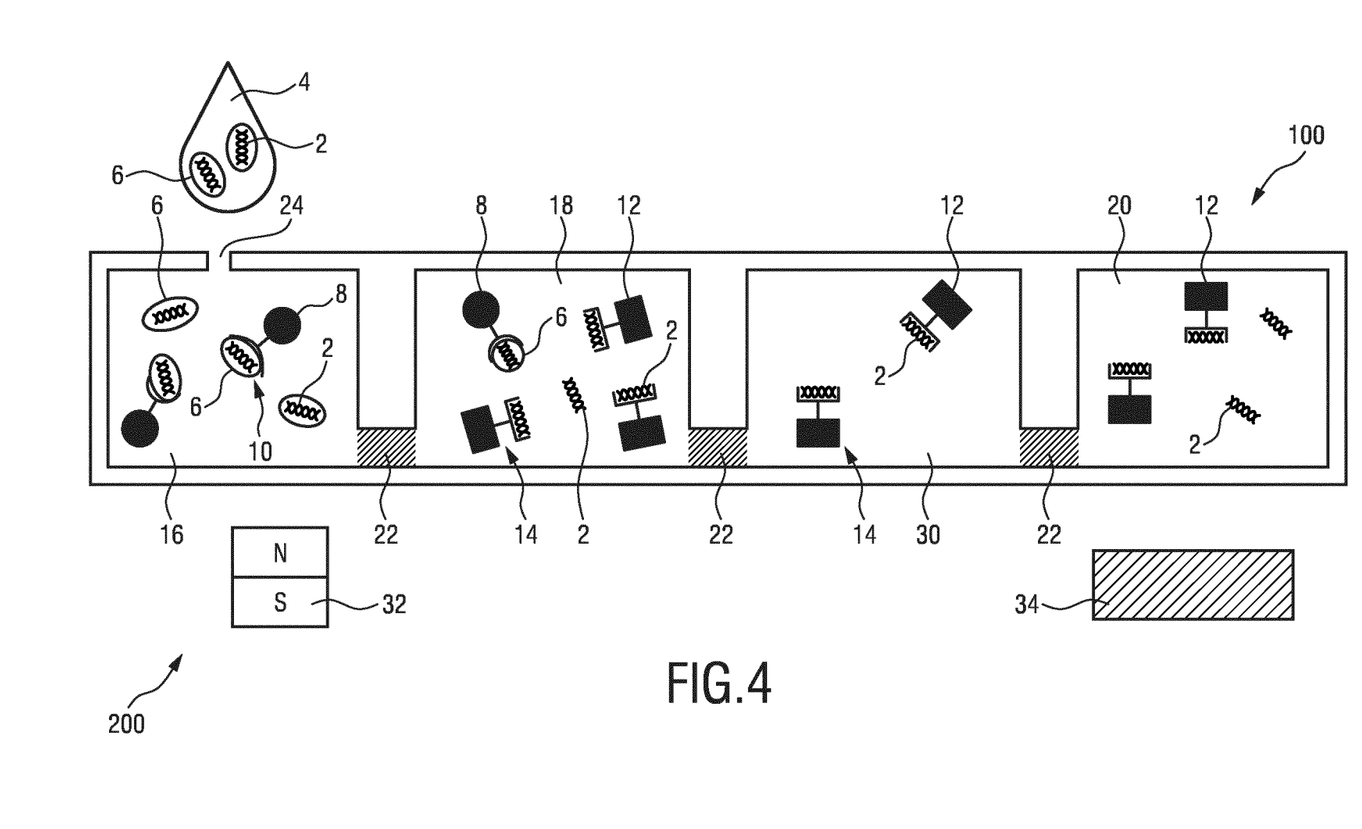
FIG. 4 shows a first embodiment of a system and device in accordance with the present invention.

FIG. 4 shows a first embodiment of a system 200 and device 100 in accordance with the present invention. In addition to the elements of the first and second embodiment of the device 100 shown in FIGS. 1 to 3 the embodiment of the system 200 further comprises a magnet 32 for moving the magnetic particles through the chambers 16, 18, 30 and 20 and a detection unit 34 for detecting the analyte 2 (bound or un-bound to the magnetic particles).

The method which can be performed in the device 100 is described above. The device 100 and system 200 may be used for isolating an analyte 2 as well as for amplifying and detecting an analyte 2. Therefore, the system 200 and the device 100 may be arranged.

An alternative method which can be performed in the device 100 may be described as follows:

In a device 100 with on-board reagents, fluids, etc., the fluid storage for the second chamber 18 may be filled with lysis buffer and magnetic silica particles. The buffer can be released from the fluid storage which is formed as a blister by piercing it under the application of pressure. In this preferable embodiment the body fluid sample 4 is sputum and the isolated target may be MTB bacteria and the analyte may be the MTB DNA.

Upon binding the MTB bacteria as a target 6 to the TB beads as a first magnetic particle 8 in the first chamber filed with liquefaction buffer, the magnetic field of a displaceable permanent magnet 32 may be used to transfer the TB particles formed as a first complex 10 into a first washing chamber.

Optionally, the TB particles 10 can now be spread out across the floor of the chamber by using a mixing magnet. When the first complex 10 reaches the second chamber 18 and the magnet 32 is removed the lysis process is initiated by emptying the contents of the fluid storage into the second chamber 18. Due to the motion of the fluid, the silica particles as a second magnetic particle 12 suspended in the lysis buffer may be distributed across the fluid chamber and can efficiently capture nucleic acids as an analyte 2 from the lysed bacteria. By filling the second chamber 18 only after transporting the TB beads 8, the magnet 32 may not disturb the suspension of silica particles 12 during the transport step.

In a further preferable embodiment, the body fluid sample 4 could include gram-negative bacteria as a target 6 that are present at low concentrations. In such a case, the device 100 could first extract with a very large amount of hydrophobic beads as a first magnetic particle 8 the bacteria from a large volume. Afterwards, a small amount of silica particles as the second magnetic particle 12 that are suitable for eventual elution in a very small volume may bind to the analyte 2. Therefore, a high up-concentration of analyte 2 is possible.

The analyte 2 which can be isolated may be a biomarker, such as peptides, proteins, hormones and preferred nucleic acids e.g. DNA. The target 6 may be a microorganism such as bacteria.

In a preferable embodiment the first magnetic particle 8 is a TB-bead and therefore binds specifically to MTB as a preferred target 6. In a further preferable embodiment the second magnetic particle 12 is a silica bead and bind thereof specific to nucleic acids as an analyte 2.

In a preferable embodiment the body fluid sample 4 is a sputum sample. Before isolating an analyte 2 this body fluid sample 4 may preferably be liquefied and therefore be homogenized. The liquefaction may be performed by a liquefaction buffer using e.g. N-acetyl-L-cysteine-sodium hydroxide (NALC-NaOH). Alternatively, the liquefaction may also be achieved by applying heat, physical disruption methods such as ultrasound, or by chemical treatment.

Figure 5:
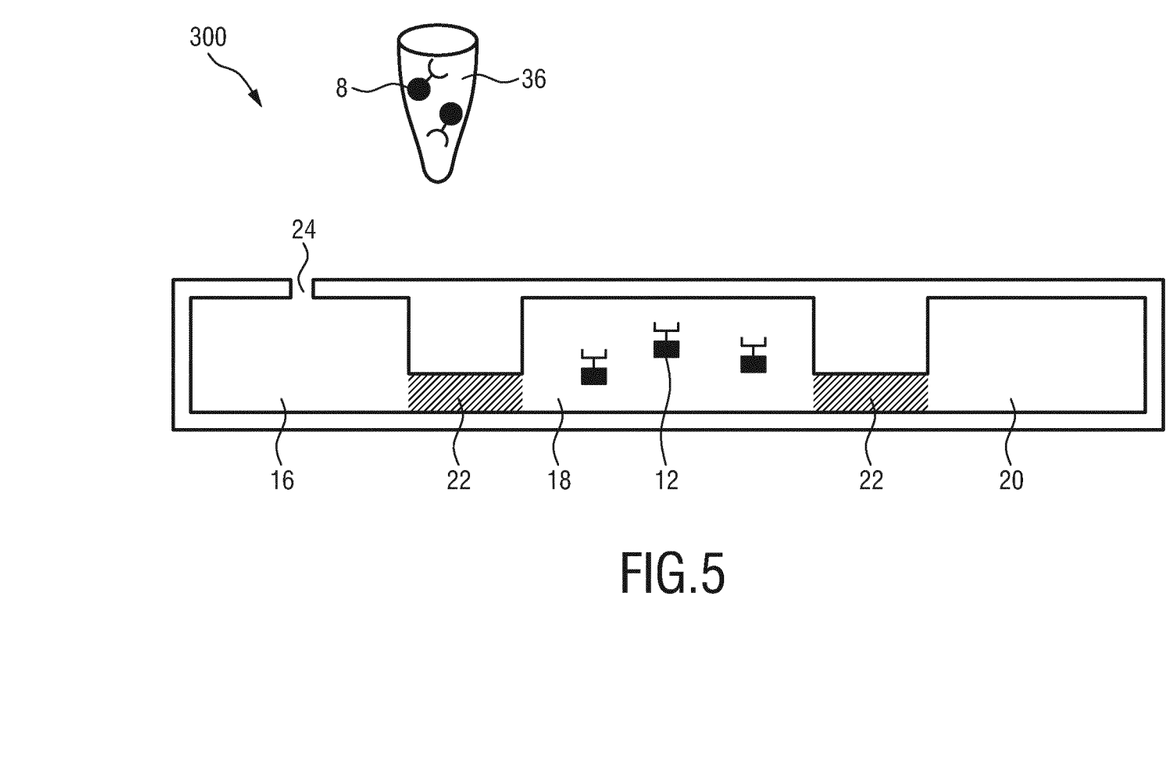
FIG. 5 shows a first embodiment of a kit in accordance with the present invention.

FIG. 5 shows a first embodiment of a kit 300 in accordance with the present invention. The kit 300 shown in FIG. 5 comprises a sample preparation chamber 36, which enables forming of the first complex 10 by binding of the first magnetic particle 8 to the target 6 in the body fluid sample 4. The kit 300 also comprises at least three chambers 16, 18, 20 arranged in series and configured to include fluids. A first chamber 16 enables forming of the first complex 10 by binding of the first magnetic particle 8 to the target 6, or the first chamber 16 enables receiving the first complex 10. A second chamber 18 enables releasing the analyte 2 from the target 6 and forming of the second complex 14 by binding of the second magnetic particle 12 to the analyte 2. A third chamber 20 enables eluting the analyte 2 from the second magnetic particle 12 and isolating the analyte 2 from the body fluid sample 4.

In a preferred embodiment the kit 300 comprises at least three chambers 16, 18 and 20. These chambers may be empty before isolating an analyte from a body fluid sample 4; therefore, the user of the kit 300 may put the magnetic particles and the fluids into the chambers.

The first chamber 16 comprises a sample inlet 24 for receiving a body fluid sample 4. In a preferred embodiment the second or third chamber 18 and 20 also comprises inlets for fluids or magnetic particles.

The main function of the at least three chambers 16, 18 and 20 is to provide an inlet, in which isolation can be performed, analogously to the device 100. The main function of the sample preparation chamber 36 is to incubate the body fluid sample 4 with the first magnetic particle 8 and, optionally, to prepare the body fluid sample 4 with a fluid e.g. a liquefaction buffer.

The at least three chambers 16, 18 and 20 as well as the sample preparation chamber 36 may have all reagents "onboard" (magnetic particles and fluids). In this preferable embodiment the first chamber 16 may comprise the first magnetic particle 8 and the second chamber 18 may comprise the second magnetic particle 12. In another embodiment of the present invention the magnetic particles are not stored in the chambers 16, 18 and 20, but are stored separately. Therefore, the user of the kit 300 may put the magnetic particles into the chambers; this also applies to the fluids. The chambers of the kit 300 may further comprise one or more fluids, which are selected from the group of buffer solutions, in particular liquefaction buffer, lysis buffer, wash buffer or elution buffer.

The first magnetic particle 8 may be stored in the sample preparation chamber 36. Further, the sample preparation chamber 36 may not be connected to the first chamber. Therefore, the user of the kit may put the body fluid sample from the sample preparation chamber 36 to the first chamber manually.

The method, which can be performed with the kit 300, is described above for the device 100 and system 200; this also applies for the use of the kit 300. An alternative method, which can be performed with the kit 300, may be described as follows:

In a first step the body fluid sample 4 e.g. sputum is incubated with the first magnetic particle. The incubation may be performed in the first chamber 16 or in the sample preparation chamber 36. Further, the body fluid sample 4 may be homogenized and liquefied by the liquefaction buffer.

Subsequently, the first type of magnetic particle 8 may bind to the target 6 to form a first complex 10. The target 6 is part of the body fluid sample 4, wherein an analyte 2 is again part of the target 6. After an incubation time, most of the first magnetic particles 8 are present as a first complex 10. In case the sample preparation chamber 36 is used, the body fluid sample 4 may be introduced into the first chamber 16. The subsequent steps are described above.

In a further preferable embodiment the device 100, the system 200 and the kit 300 may be used as a rapid, robust and easy to use point-of-care diagnostic assay for small sample volumes. The isolation and the subsequent detection of a biomarker (analyte) may be performed either directly at the bedside, or at the physician's office or even at home.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

The invention claimed is:

1. A device for isolating an analyte from a body fluid sample, wherein the analyte is part of a target contained in the body fluid sample, said device comprising:

at least two types of magnetic particles, wherein a first type of magnetic particle is capable to bind the target to form a first complex for purifying the target from the body fluid sample, and wherein a second type of magnetic particle is capable to bind the analyte contained in the target to form a second complex for isolating the analyte;

at least three chambers, arranged in series and configured to include fluids, to allow controlled movement of the magnetic particles, and to prevent the mixing of fluids, wherein a first chamber enables forming of the first complex by binding of the first type of magnetic particle to the target, wherein a second chamber enables releasing the analyte from the target and forming of the second complex by binding of the second type of magnetic particle to the analyte, and wherein a third chamber enables eluting the analyte from the second type of magnetic particle and isolating the analyte from the body fluid sample;
an inlet for the introduction of the body fluid sample to one of the chambers; and
at least one fluid for releasing the analyte from the target.

2. The device according to claim 1, wherein the chambers are connected via magneto-capillary valves through which the magnetic particles can controllably be moved.

3. The device according to claim 1, further comprising one or more fluids selected from the group consisting of liquefaction buffer, lysis buffer, wash buffer and elution buffer.

4. The device according to claim 1, further comprising fluid storages connected to the chambers for storing fluids or magnetic particles.

5. The device according to claim 4, wherein the at least one fluid is a lysis buffer for lysing the target to release the analyte stored in the second chamber or in a fluid storage connected to the second chamber.

6. The device according to claim 4, wherein the first type of magnetic particle is stored in the first chamber or in a fluid storage connected to the first chamber or wherein the second type of magnetic particle is stored in the second chamber or in a fluid storage connected to the second chamber.

7. The device according to claim 1, wherein the analyte is selected from the group consisting of proteins, antibodies, lipids, enzymes, nucleic acids and any mixture thereof or wherein the target is selected from the group consisting of cells, viruses, and bacteria.

8. The device according to claim 1, wherein the first type of magnetic particle has a hydrophobic coating for binding *Mycobacterium Tuberculosis*, and the second type of magnetic particle has a silica coating for binding nucleic acids.

9. The device according to claim 1, wherein the body fluid sample is selected from the group consisting of sputum, blood, plasma, serum, lactation products, amniotic fluids, saliva, urine, semen, cerebrospinal fluid, bronchial aspirate, perspiration, mucus, liquefied stool sample, synovial fluid, lymphatic fluid, tears, tracheal aspirate, and any mixture thereof.

10. The device according to claim 1, further comprising a fourth chamber, in which the first or second complex can be washed.

11. A system for isolating an analyte from a body fluid sample, wherein the analyte is part of a target contained in the body fluid sample, said system comprising:
a device as claimed in claim 1 for isolating the analyte from the body fluid sample; and
a magnet for applying a magnetic field to controllably move the magnetic particles through the chambers.

12. A system according to claim 11, further comprising a detection unit for detecting the magnetic particles, bound to the target or analyte, wherein the detection unit detects the analyte bound to the second type of magnetic particle.

13. A method for isolating an analyte from a body fluid sample, wherein the analyte is part of a target contained in the body fluid sample, said method comprising:
receiving the body fluid sample, wherein the body fluid sample comprises the target, which contains the analyte; and
performing an isolation of the analyte from said body fluid sample by:
binding of a first type of magnetic particle to the target to form a first complex in a first chamber;
moving the first complex from the first chamber to a second chamber;
releasing the analyte from the target;
binding of a second type of magnetic particle to the analyte to form a second complex in the second chamber;
moving the second complex from the second chamber to a third chamber; and
eluting the analyte from the second complex for isolating the analyte.

14. A kit for isolating an analyte from a body fluid sample, wherein the analyte is part of a target contained in the body fluid sample, said kit comprising:
at least two types of magnetic particles, wherein a first type of magnetic particle is capable to bind the target to form a first complex for purifying the target from the bodyfluid sample, and wherein a second type of magnetic particle is capable to bind the analyte contained in the target to form a second complex for isolating the analyte;
at least one or more fluids which are selected from the group consisting of liquefaction buffer, lysis buffer, wash buffer and elution buffer; and
at least three chambers arranged in series and configured to include fluids, to allow controlled movement of the magnetic particles, and to prevent the mixing of fluids, wherein a first chamber enables forming of the first complex by binding of the first type of magnetic particle to the target, or the first chamber enables receiving the first complex, wherein a second chamber enables releasing the analyte from the target and forming of the second complex by binding of the second type of magnetic particle to the analyte, and wherein a third chamber enables eluting the analyte from the second type of magnetic particle and isolating the analyte from the body fluid sample.

15. The kit according to claim 14, further comprising a sample preparation chamber, wherein the sample preparation chamber enables forming of the first complex by binding of the first type of magnetic particle to the target in the body fluid sample.

* * * * *